US011366337B2

(12) United States Patent
Limon et al.

(10) Patent No.: US 11,366,337 B2
(45) Date of Patent: Jun. 21, 2022

(54) OPTICAL LENS WITH HALO REDUCTION

(71) Applicant: Brien Holden Vision Institute Limited, Sydney (AU)

(72) Inventors: Ofer Limon, Kfar-Saba (IL); Zeev Zalevsky, Rosh HaAyin (IL); Alex Zlotnik, Ashdod (IL); Shai Ben-Yaish, Nechalim (IL)

(73) Assignee: Brien Holden Vision Institute Limited, Sydney (AU)

( * ) Notice: Subject to any disclaimer, the term of this patent is extended or adjusted under 35 U.S.C. 154(b) by 0 days.

(21) Appl. No.: 16/848,097

(22) Filed: Apr. 14, 2020

(65) Prior Publication Data
US 2020/0310158 A1 Oct. 1, 2020

Related U.S. Application Data

(63) Continuation of application No. 14/367,389, filed as application No. PCT/IL2012/050538 on Dec. 20, 2012, now Pat. No. 10,656,437.

(60) Provisional application No. 61/578,401, filed on Dec. 21, 2011.

(51) Int. Cl.
*G02C 7/02* (2006.01)
*A61F 2/16* (2006.01)

(52) U.S. Cl.
CPC ........ *G02C 7/02* (2013.01); *A61F 2002/1699* (2015.04)

(58) Field of Classification Search
CPC ............ A61F 2002/1699; A61F 2/1613; A61F 2/1618; A61F 2/1637; A61F 2/164; A61F 2/1648; A61F 2/1654; G02C 7/02; G02C 7/028; G02C 7/044; G02C 7/042; G02C 2202/20; G02B 3/10; G02B 3/08; G06F 7/00; G06F 17/00
USPC ............ 351/159.01, 159.02, 159.05, 159.06, 351/159.09–159.16, 159.2, 351/159.41–159.44, 159.55; 623/6.27–6.29, 6.32, 6.33
See application file for complete search history.

(56) References Cited

U.S. PATENT DOCUMENTS 5,096,285 A 3/1992 Silberman
5,767,940 A 6/1998 Hayashi
6,210,005 B1 4/2001 Portney
(Continued)

FOREIGN PATENT DOCUMENTS

EP 2098192 9/2009
EP 2098192 A1 * 9/2009 ............. G02C 7/044
(Continued)

OTHER PUBLICATIONS https://www.merriam-webster.com/dictionary/periodice (year: 2010).

*Primary Examiner* — Travis S Fissel
(74) *Attorney, Agent, or Firm* — Jones Day

(57) ABSTRACT

A method is provided for use in reducing a size of halo effect in an ophthalmic lens. The method comprises: providing data indicative of a given ophthalmic lens with a first pattern providing prescribed vision improvement, processing said data indicative of the features of the first pattern and generating data indicative of a variation of at least one feature of the first pattern resulting in a second pattern which maintains said prescribed vision improvement and reduces a size of halo effect as compared to that of the lens with the first pattern.

15 Claims, 17 Drawing Sheets

(56) References Cited

U.S. PATENT DOCUMENTS

| | | |
|---|---|---|
| 6,557,998 B2 | 5/2003 | Portney |
| 7,061,693 B2 | 6/2006 | Zalevsky |
| 7,284,861 B2 | 10/2007 | Fujieda |
| 7,812,295 B2 | 10/2010 | Zalevsky et al. |
| 7,857,451 B2 | 12/2010 | Thibox |
| 7,879,089 B2 | 2/2011 | Hong |
| 8,169,716 B2 | 5/2012 | Zalevsky |
| 9,329,407 B2 | 5/2016 | Cathey et al. |
| 2003/0008149 A1 | 1/2003 | Moravec |
| 2003/0081174 A1* | 5/2003 | Ross .................... A61B 3/0025 |
| | | 351/212 |
| 2005/0094100 A1 | 5/2005 | Ross |
| 2005/0203619 A1 | 9/2005 | Altmann |
| 2006/0098163 A1 | 5/2006 | Bandhauer |
| 2006/0203198 A1 | 9/2006 | Liang |
| 2007/0121101 A1 | 5/2007 | Hinderling |
| 2007/0236769 A1* | 10/2007 | Zalevsky ........... G02B 27/0075 |
| | | 359/238 |
| 2008/0033546 A1* | 2/2008 | Liang .................... A61F 2/1613 |
| | | 623/5.11 |
| 2009/0268158 A1 | 10/2009 | Weeber |
| 2010/0007957 A1 | 1/2010 | Suzuki |
| 2010/0165134 A1 | 7/2010 | Dowski |
| 2010/0238400 A1 | 9/2010 | Volk |
| 2011/0043751 A1 | 2/2011 | Blum |
| 2011/0270586 A1 | 11/2011 | Weeber |

FOREIGN PATENT DOCUMENTS

| | | | |
|---|---|---|---|
| WO | WO 2007/133384 | 11/2007 | |
| WO | WO-2007133384 A2 * | 11/2007 | ............. G02C 7/042 |
| WO | WO 2012/085917 | 6/2012 | |

* cited by examiner

OPTICAL LENS WITH HALO REDUCTION

CROSS REFERENCE TO RELATED APPLICATION

This application is a continuation of U.S. application Ser. No. 14/367,389, filed Jun. 20, 2014, which is the National Phase application of International Application No. PCT/IL2012/050538, filed Dec. 20, 2012, which claims benefit to U.S. Provisional Application No. 61/578,401, filed Dec. 21, 2011, which designates the United States and was published in English. These applications, in their entirety, are incorporated herein by reference.

TECHNOLOGICAL FIELD AND BACKGROUND

The present invention is generally in the field of ophthalmic lenses, including contact lenses and intraocular lenses, and relates to such lenses with reduced halo effects.

Halo effects are known as a glow or color light pattern that can be best observed when looking at a bright source in front of a dark background, for example a broad spot of light seen around a street light in the dark. This optical phenomenon is mainly caused by interaction of light with matter, and is enhanced due to diffraction of light when interacting with the eye, e.g. passing through the eye pupil, eye tissue, or any other diffraction of light caused by sharp edges or artificial diffraction structures, such as intraocular lens.

Techniques aimed at reducing the halo effects in lenses have been developed. For example, U.S. Pat. No. 6,557,998 discloses ophthalmic lenses, for example, intraocular lenses, contact lenses, corneal implant lenses and the like, having multifocal characteristics which provide beneficial reductions in at least the perception of one or more night time visual symptoms such as "halos", and "glare or flare". According to this technique, an intraocular lens having a baseline diopter power for far vision correction, has a near zone including an inner region having a substantially constant vision correction power greater than the baseline diopter power, and an additional near zone located outwardly of the near zone and having vision correction powers greater than the baseline diopter power and the near zone, and including a central plateau region having an inner end and an outer end and vision correction powers which increase progressively from the inner end to the outer end.

GENERAL DESCRIPTION

The present invention provides a novel configuration of an ophthalmic lens, as well as a method of designing such lens, which, on the one hand, maintains the patient's prescribed vision improvement and, on the other hand, reduces a size of halo effect.

The present invention is in particular useful for improving lenses having certain pattern (first pattern) corresponding to the patient's prescribed vision improvement, for example a pattern aimed at extending the depth of focus (EDOF) of an ophthalmic lens such as to enable the lens to improve both the near and far visions of a patient, rather than using a bi-focal or multi-focal lens. Such a first pattern is typically to be produced on the lens surface in a surface relief in the form of an array of protrusions-and-pits. Generally, however, it is phase pattern formed by spaced-apart regions of different optical properties, which alternatively to the protrusions-and-pits pattern may be in the form of spaced-apart regions of different refractive index materials, e.g. by embedding a different material into the spaced-apart surface regions of the lens.

According to the invention, data indicative of the features of such first pattern for a given lens is used for determining variation(s) of at least one feature of the first pattern resulting in a second pattern, which maintains the prescribed vision improvement and reduces a size of halo effect as compared to that of the lens with the first pattern. Then, the lens surface can be processed to form said second pattern thereon.

The first pattern is typically a periodic pattern. The second pattern may be periodic or not. The at least one feature of the first pattern that is altered/varied may include one or more of the following: width and/or depth of spaced-apart features, period, pitch, local transition (e.g. smoothness and slope at an interface between regions of different optical properties, such as location of slope variation or interface between regions generating different phases), local slope/curvature, as well as any other feature of the type affecting the periodicity of the first pattern. As indicated above, the first pattern may be configured as EDOF pattern. This may be a substantially non-diffractive phase pattern (i.e. the pattern features are arranged on the lens surface with low spatial frequency with regard to wavelengths of visual spectrum), for example as described in the following patent publications U.S. Pat. No. 7,061,693, WO 12/085917, U.S. Pat. Nos. 8,169,716, 7,812,295, all assigned to the assignee of the present application.

The present invention is based on the inventors' understanding of the following: The ability of the human eye to observe the halo pattern is due to the logarithmic response of the human eye. Light passage through a periodic structure, and in particular a periodic phase structure, typically results in certain interference/diffraction pattern such as color rings structure on the imaging plane, which is typically of relatively low intensity. Due to the fact that the human eye has logarithmic response to light, when observing a light source over dark background (e.g. looking at a street light at night), such interference/diffraction pattern is seen as a halo effect around the light source. Considering the phase pattern as a combination of several amplitude sinusoidal functions, where the frequency of each sinusoidal function is a native multiplication of the original frequency of the phase pattern, the inventors of the present invention have found that by breaking the periodicity of the phase pattern, the pattern could no longer be described as a summation of sinusoidal functions with the same base frequency, but rather with different base frequencies. This will result, with the proper parameters of the combined pattern, in elimination of the arc color rings. The proper selection of the pattern parameters (second pattern) includes altering of the feature(s) of the first pattern to obtain one or more of the following: (i) deviation from a local period of the first pattern; (ii) deviation from a local slope of the first pattern (inner and outer slope); (iii) deviation from local maximum height of protrusions in the first pattern; (iv) deviation from local minimum height of protrusions in the first pattern; (v) producing additional, typically highly dense, pattern within one type of features of the first pattern; and (vi) deviation from local pattern position. Also, the first pattern may be altered by producing additional, typically highly dense, pattern within one type of features of the first pattern, e.g. within the protrusions.

The present invention provides the reduction of the size of halo effect at least by 25%.

Thus, according to one aspect of the present invention, there is provided a method for designing an ophthalmic lens with a reduced size of halo effect, the method comprising:

providing data indicative of a given ophthalmic lens with a first pattern providing prescribed vision improvement, processing said data indicative of the features of the first pattern and generating data indicative of a variation of at least one feature of the first pattern resulting in a second pattern which maintains said prescribed vision improvement and reduces a size of halo effect as compared to that of the lens with the first pattern.

Said processing of said data indicative of the features of the first pattern may comprise estimating a halo pattern of the ophthalmic lens with the first pattern.

According to some embodiments of the inventions said providing of the data indicative of the ophthalmic lens with the first pattern comprises using data indicative of at least a dimension of an effective aperture of the lens and data indicative of prescribed vision improvement, and generating data indicative of features of the first pattern to be produced on the lens to thereby provide said prescribed vision improvement.

According to another broad aspect of the invention, there is provided an ophthalmic lens comprising a surface pattern being a modification of a first pattern which is configured for providing prescribed vision improvement, at least one of features of said surface pattern being a modification of at least one feature of the first pattern such that said prescribed vision improvement is maintained and a size of halo effect is reduced as compared to that of said lens with the first pattern.

According to yet another aspect of the invention, there is provided a system for use in designing an ophthalmic lens providing prescribed vision improvement for a patient, the system comprising a control unit comprising data input utility for receiving input data indicative of the patient's vision and of desired vision improvement, and a processor utility for processing the input data and generating data indicative of a surface pattern to be produced on the lens, said processing comprising:

analyzing the input data and generating data indicative of a first pattern to be formed on the surface of the lens to provide desired vision improvement;

analyzing data indicative of the lens having said first pattern, evaluating a size of hallo effect of the lens with the first pattern, and generating data indicative of a change in at least one feature of the first pattern resulting in a second pattern which maintains said desired vision improvement and has a reduced size of halo effect as compared to that of said lens with the first pattern.

According to yet another aspect of the invention, there is provided a system for use in designing an ophthalmic lens providing prescribed vision improvement for a patient, the system comprising a processor utility for receiving and processing input data indicative of a certain first pattern to be produced on the lens surface to provide desired vision improvement, said processing comprising:

analyzing data indicative of the lens having said first pattern, evaluating a size of hallo effect of the lens with the first pattern, and generating data indicative of a change in at least one feature of the first pattern resulting in a second pattern which maintains said desired vision improvement and has a reduced size of halo effect as compared to that of said lens with the first pattern.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 12A shows the first pattern and FIG. 12B shows an optimized second pattern;

DETAILED DESCRIPTION OF EMBODIMENTS

Figure 1A:
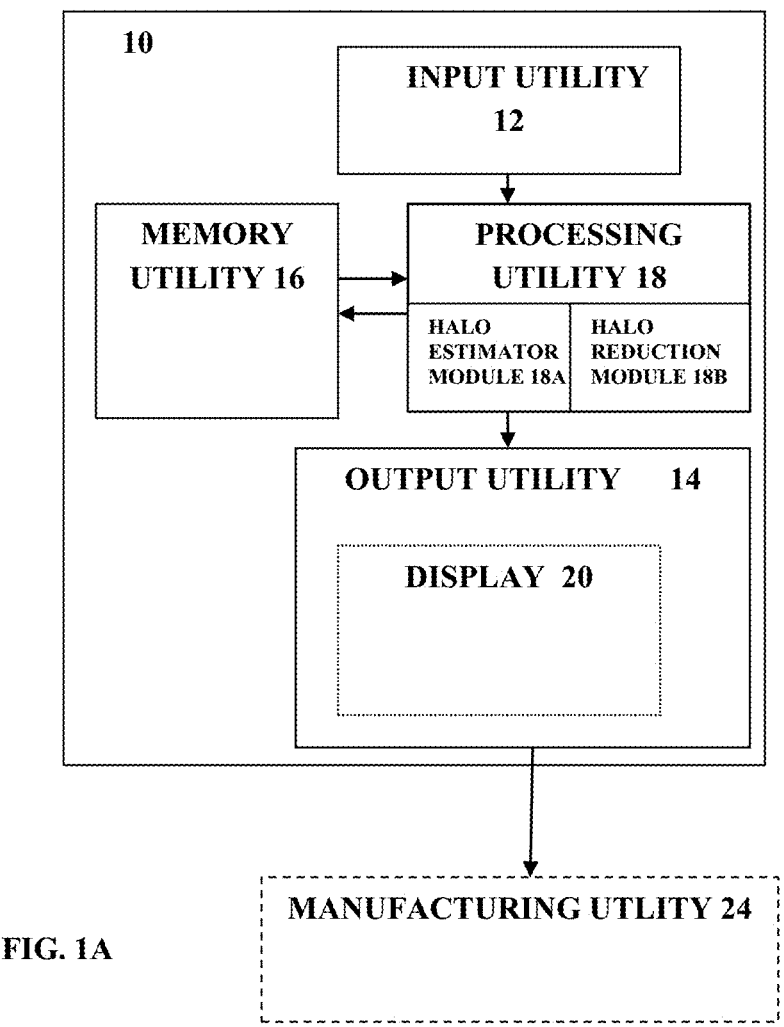
FIG. 1A is a schematic illustration of a system according to the invention for designing an ophthalmic lens.

Referring to FIG. 1A, there is illustrated, by way of a block diagram, a system 10 of the present invention configured and operable for designing an ophthalmic lens providing prescribed vision improvement for a patient. The system 10 is typically a computer system including inter alia such main functional utilities as data input and output utilities 12 and 14, memory utility 16, data processing and analyzing utility 18 and possibly also a display 20. The system 10 is configured and operable to design, or assist in designing, ophthalmic lenses with reduced halo pattern effect while providing prescribed vision improvement for various patients. The system 10 may receive, via the data input utility 12, data about prescribed vision improvement for a given ophthalmic lens of a patient (such as certain extension of depth of focus) to be used to determine a first vision improvement pattern on the lens surface, or such data may include the first pattern data providing such vision improvement. The input data is properly processed by the processing utility 18 to design such given lens which is characterized by the prescribed vision improvement and reduced halo effect. Thus, optionally, the processing utility 18 operates to first determine the first pattern data in accordance with the prescribed vision improvement, possibly using various recorded patterns stored in the memory utility 16. The processing utility 18 includes a halo estimator module 18A which analyzes the lens with the first pattern and calculates the parameters/profile of halo effect resulting from the first pattern. The processing utility 18 further includes a halo reduction module 18B which operates to analyze the halo effect of the lens with the first pattern and the optical properties (features) of the first pattern (e.g. responsible for the prescribed vision improvement), identify the proper variations to be introduced to the first pattern (at least one feature thereof) to minimize the halo effect, and then generate data indicative of a corresponding second pattern. The latter includes the modified first pattern, i.e. first pattern with the calculated variations thereof thus having minimized halo effect while maintaining the prescribed vision improvement.

This data indicative of the second pattern may then be used by a manufacturing unit 24 (patterning equipment), for producing an ophthalmic lens having the second pattern. The data indicative of the second pattern or of a given lens with the second pattern (as the case may be) may be stored in the memory utility 16 for later use. Additionally, various parameters of the first pattern, modifications thereof or the second pattern may be presented to an operator via the display 20 to provide control over the processing and enable human selection of parameters.

It should be noted that considering the EDOF-based first pattern as described in the above-listed patent publications U.S. Pat. No. 7,061,693, WO 12/085917, U.S. Pat. Nos. 8,169,716, 7,812,295 assigned to the assignee of the present application, the EDOF pattern parameters may practically be defined only by the physical dimension of the lens, i.e. its effective aperture, and thus being more or less universal for lenses with different optical powers, or optical power distributions. In such cases, where the first pattern(s) can be well defined for given lenses, the present invention provides for creating a database including data about various lenses for prescribed improved vision together with the data about corresponding second patterns (modified first pattern).

As indicated above, the intensity pattern of the halo effect is orders of magnitude weaker than the illumination intensity peak. However, the human eye has unique nature in response to light, relative to industrial light detectors, and provides logarithmic response. The present invention enables simulating of a halo pattern as observed by the human eye. To generate such a simulated halo pattern, the processing utility 18 may be configured (preprogrammed) to model the photopic response of a human eye with a set of at least 3 wavelengths covering the visible spectrum and appropriately adjusted and with appropriate relative weights. Typically, the wavelengths are selected to emphasize the peak in human vision spectrum, i.e. selection of the wavelengths may be centered around a primary wavelength of 540 nm. It should be noted that the model may be smoother and more reliable if it is based on a higher number of wavelengths or wavelength ranges; typically the use of 7 different wavelengths may provide sufficient result.

In order to facilitate calculations, the processing utility may generate, or access from the memory utility 16, a look up table including relations between the modeled wavelengths and RGB spectrum. Table 1 below exemplifies such wavelength to RGB ratio look up table, illustrating relative weights of certain wavelengths in the primary RGB colors. The RGB look up table data may be transformed and normalized to count for the modeled photopic spectrum. This is typically needed to provide a reliable and meaningful display of the simulated results on the display 20.

TABLE 1

| λ(μm) | w(weight) | $C_R$ | $C_G$ | $C_B$ |
| --- | --- | --- | --- | --- |
| 0.463 | 0.1574 | 0 | 133 | 255 |
| 0.488 | 0.1539 | 0 | 250 | 255 |
| 0.513 | 0.4903 | 15 | 255 | 0 |
| 0.538 | 1 | 106 | 255 | 0 |
| 0.5630 | 0.8122 | 197 | 255 | 0 |
| 0.588 | 0.3263 | 255 | 220 | 0 |
| 0.613 | 0.0570 | 255 | 122 | 0 |

The processing utility may produce a high dynamic range PSF (Point Spread Function) for each of the modeled wavelengths. The PSF is configured in accordance with passage of light of the associated wavelength through a lens having a certain surface pattern.

A polychromatic halo effect is calculated by summation of all PSFs calculated for different wavelengths into RGB PSF matrices, each corresponding to a single color (Red, Green or Blue). The RGB PSF matrices may be calculated by weighting and translating the proper wavelengths' PSF in accordance with the wavelength-to-RGB look up table, for example in accordance with equations 1-3 below:

$$\text{linear } psf = \sum_i w_i * psf(\lambda_i) \qquad \text{(equation 1)}$$

$$\text{linear } psf = \sum_i psf(Color_i) \qquad \text{(equation 2)}$$
$$= psf(\text{red}) + psf(\text{Green}) + psf(\text{Blue})$$

$$psf(Color_i) = \frac{\sum_j w_j * C_i(\lambda_j) * psf(\lambda_j)}{\sum_k C_i \lambda_k} \qquad \text{(equation 3)}$$

Here $w_i$ corresponds to the weight of wavelength $\lambda_i$ in the spectrum, and the parameters $C_i(\lambda_j)$ correspond to the Red/Green/Blue coefficients for wavelength $\lambda_j$ as shown e.g. in look up table 1. To simulate the logarithmic response of the human eye the processing utility may operate to calculate a logarithmic scale of the combined PSF:

$$\text{Log } psf = \log_{10}(\text{linear } psf) \qquad \text{(equation 4)}$$

An appropriate cutoff threshold may be applied to the logarithmic PSF, as well as root square or similar modification to intensify the low intensities and scale the logarithmic PSF into a linear desired range appropriate for display and calculations, e.g. standard RGB range ([0,1] or [0,255]). The resulting pattern provides a simulated halo effect as seen by a human eye using a given ophthalmic lens having said surface pattern. Results of such simulation can be displayed via the display unit 20 to provide comprehensible indication on the size of the halo pattern/effect and required/desired reduction thereof.

Figure 1B:
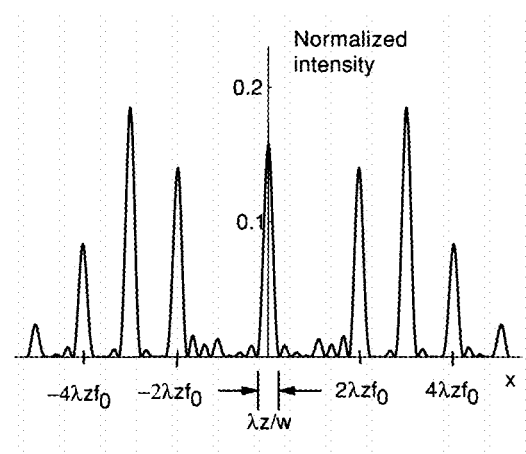
FIG. 1B exemplifies a normalized intensity profile for a ring-like pattern producing halo effect in polychromatic illumination.
Figure 2:
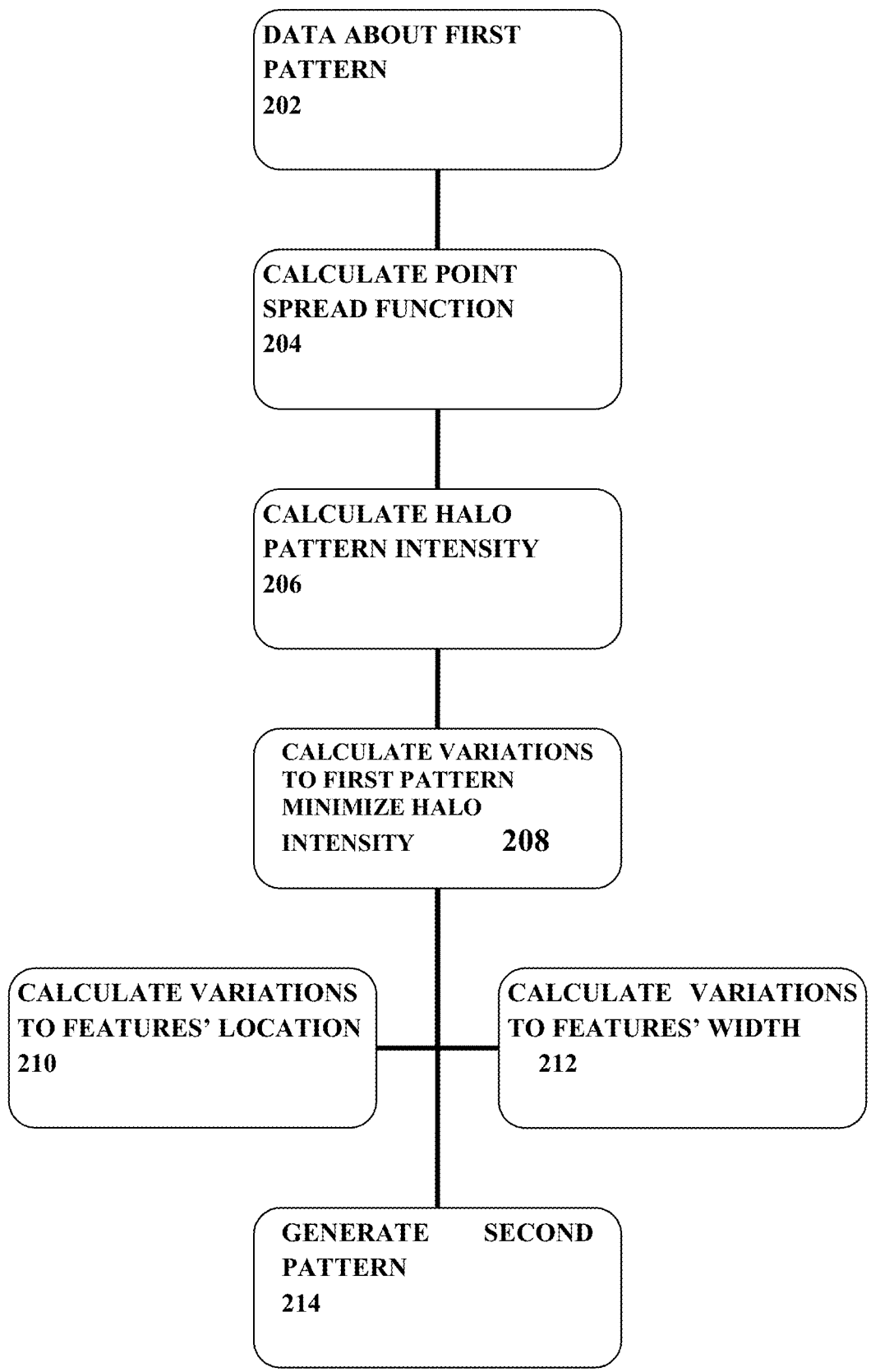
FIG. 2 is a flow chart of an example of a method of the invention for designing an ophthalmic lens.

As indicated above, a periodic phase structure may cause color rings structure on the imaging plane when imaging a small light source over a relatively dark background. This color rings structure, although having very low intensity relative to the bright light source, generates a noticeable halo pattern when viewed in a logarithmic scale (e.g. when the imaging plane is the retina of a human eye). This physical phenomenon can be easily explained by describing the phase structure of the lens as a thin sinusoidal phase pattern at the aperture, and transforming it to describe a point spread function (PSF) at the imaging plane by using the Fraunhofer approximation. The amplitude transmittance function describing a fast finite sinusoidal phase structure in the aperture may be described as:

$$t_A(\xi, \eta) = \exp\left[j\frac{m}{2}\sin(2\pi f_0 \xi)\right] rect\left(\frac{\xi}{2w}\right) rect\left(\frac{\eta}{2w}\right) \qquad \text{(equation 5)}$$

where $f_0$ is the spatial frequency of the structure, w is the aperture width and m represents the peak-to-peak excursion of the phase delay. The intensity pattern generated by light from a monochromatic a point source illumination passing through the above described phase pattern is given by:

$$I(x, y) \cong \left(\frac{A}{\lambda z}\right)^2 \sum_{q=-\infty}^{\infty} J_q^2\left(\frac{m}{2}\right) sinc^2\left[\frac{2w}{\lambda z}(x q f_0 \lambda z)\right] sinc^2\left(\frac{2wy}{\lambda z}\right) \qquad \text{(equation 6)}$$

where $J_q^2$ is a Bessel function of the first kind, order q, z is the distance from the phase pattern to the imaging plane and A is the amplitude of the light. An example of intensity pattern generated on the image plane due to light passage through the phase structure described in equation 5 above is shown in FIG. 1B. As shown, the intensity pattern includes for a certain wavelength a set of distinct intensity peaks having specific width and spacing resulting from periodicity of the structure. A broadband/polychromatic illumination would sum up a displaced intensity pattern for each wavelength. This would yield an arc of colorful rings Reference is made to FIG. 2, showing a flow chart diagram of an example of the data processing method of the invention, e.g. carried out by the above-described processing utility 18. As shown, the processing includes receiving data indicative of the first pattern 202, this data may include a structure of the first pattern and/or data about desired vision improvement sufficient for designing said first pattern. Typically, the processing may include calculation of a polychromatic or monochromatic point spread function (PSF) 204 associated with the first pattern and proper imaging conditions. In order to assess size of halo pattern generated by a lens having the first pattern, the processing may include calculation of the halo pattern intensity 206 as described above. As noted, this calculation may be based on at least three wavelengths, and preferably on seven wavelengths of the visible spectrum.

To minimize the Halo pattern the processing utility operates to calculate variations to the first pattern 208. The variation may be aimed at altering the periodicity of the first patter, which may for example include variations of the relative location of the different features of the first pattern 210 and/or variation of parameters of the features such as the width 212 of certain features. It should be noted that other pattern related and/or feature related parameters may be used for optimization of the pattern to minimize the generated halo pattern. The principles behind the variation calculation is based on the inventor's understanding that by breaking the periodicity of the phase structure, the structure can no longer be described as a summation of sinusoidal function with the same base frequency, but rather with different base frequencies. Using the simplification of equation 6 above with selection of the proper parameters will result in elimination of the arc color rings, and reduction of the generated halo pattern. The second pattern is selected as the pattern resulting from the variation/modification of the first pattern which minimizes the halo pattern. Thus, data indicative of the second pattern is generated in step 214 to be output for further use (e.g. manufacturing).

According to some embodiments of the present invention, the processing utility may operate to apply the minimizing process as follows: the first pattern is characterized as phase profile along the surface of the lens (or a corresponding optical element) including possible variations of certain parameters. A halo pattern is calculated according to the first phase pattern, and is then minimized by variations of the selected parameters until a minimum is selected providing the parameters for the second pattern.

For example, assuming a binary multi ring phase element, e.g. EDOF element, which can be described as:

$$g(x) = \sum_n \left( \exp(ia_n) rect\left(\frac{x - n\Delta x - \delta x_n}{W_n}\right) - rect\left(\frac{x - n\Delta x - \delta x_n}{W_n}\right) \right) + \qquad \text{(equation 7)}$$

$$rect\left(\frac{x}{W_T}\right)$$

$$= \left(\sum_n (\exp(ia_n) - 1) rect\left(\frac{x - n\Delta x - \delta x_n}{W_n}\right)\right) +$$

$$rect\left(\frac{x}{W_T}\right)$$

where $W_n$ is the width of each phase groove/feature, $\Delta x$ is the distance between adjacent features and $\delta x_n$ define variations in the location of each feature, i.e. the deviation of the periodicity of the pattern resulting from changes in the position of each groove/feature. The overall size of the phase pattern is $W_T$ which actually describes the full aperture of the corresponding lens/optical element. This non-limiting example is based on the assumption that the phases $a_n$ of all features are equal and can thus be replaced by $a_0$, it should however be noted that this assumption is used to simplify the analytic calculations and the same technique may be utilized for features providing different phases. Thus the first pattern may be described as:

$$g(x) = \left((\exp(ia_0) - 1)\sum_n rect\left(\frac{x - n\Delta x - \delta x_n}{W_n}\right)\right) + rect\left(\frac{x}{W_T}\right) \quad \text{(equation 8)}$$

As indicated above, to calculate the halo pattern generated by imaging a point source by an optical element carrying the first pattern (e.g. pattern of equation 8) the processing may include calculation of the PSF associated with first phase pattern. Generally (for monochromatic illumination) the PSF can be calculated as the Fourier transform of the phase pattern providing:

$$p(\mu) = \int g(x)\exp(2\pi i x \mu)dx \quad \text{(equation 9)}$$

$$= (\exp(ia_0) - 1)\left(\frac{\sum_n W_n \text{sinc}(W_n\mu)\exp}{(2\pi i\mu(n\Delta x + \delta x_n))}\right) +$$

$$W_T \text{sinc}(W_T\mu)$$

As generally known, the PSF is defined as a response of an optical element to illumination by a point source, i.e. the image generated on a corresponding imaging plane. Typically, the PSF, as calculated above for monochromatic illumination, describes the field generated by the point source and not the intensity. The intensity pattern itself for all the diffraction orders, is given by:

$$I_{Halo} = \sum_m \left|p\left(\frac{m}{\Delta x}\right)\right|^2 = |\exp(ia_0) - 1|^2 \quad \text{(equation 10)}$$

$$\left(\sum_m \left|\sum_n W_n \text{sinc}\left(W_n\frac{m}{\Delta x}\right)\exp\left(2\pi i\frac{m}{\Delta x}(n\Delta x + \delta x_n)\right)\right|^2\right)$$

$$= |\exp(ia_0) - 1|^2$$

$$\sum_m \left(\left(\sum_n W_n \text{sinc}\left(W_n\frac{m}{\Delta x}\right)\exp\left(2\pi i\frac{m}{\Delta x}\delta x_n\right)\right)\cdot\cdot\right.$$

$$\left.\left(\sum_k W_k \text{sinc}\left(W_k\frac{m}{\Delta x}\right)\exp\left(-2\pi i\frac{m}{\Delta x}\delta x_k\right)\right)\right) =$$

$$\sum_n \sum_k \left(\sum_m W_n W_k \text{sinc}\left(W_n\frac{m}{\Delta x}\right)\text{sinc}\left(W_k\frac{m}{\Delta x}\right)\right.$$

$$\left.\exp\left(\frac{2\pi i m(\delta x_n - \delta x_k)}{\Delta x}\right)\right)$$

It can be seen that the expression within the double summation, i.e.

$$\sum_m W_n W_k \text{sinc}\left(W_n\frac{m}{\Delta x}\right)\text{sinc}\left(W_k\frac{m}{\Delta x}\right)\exp\left(\frac{2\pi i m(\delta x_n - \delta x_k)}{\Delta x}\right)$$

can be described as a Discrete Fourier Transform (DFT) of the function:

$$\psi_m(n, k) \equiv W_n W_k \text{sinc}\left(W_n\frac{m}{\Delta x}\right)\text{sinc}\left(W_k\frac{m}{\Delta x}\right) \quad \text{(equation 11)}$$

calculated at the coordinate $(\delta x_n - \delta x_k)$. Using this identity, the intensity of the halo pattern is given by:

$$I_{Holo} = \sum_n \sum_k \sum_m \psi_m(n, k)\exp\left(\frac{2\pi i m(\delta x_n - \delta x_k)}{\Delta x}\right) = \quad \text{(equation 12)}$$

$$\sum_n \sum_k \tilde{\psi}(\delta x_n - \delta x_k)$$

where $\tilde{\psi}(\delta x_n - \delta x_k)$ is the DFT of $\psi_m(n, k)$.

As indicated above, the processing is aimed at generating a second pattern configured to minimize the halo pattern. It should be noted that the intensity field as described in equations 10-13 includes the main illumination lobe (the image of the light source) as well as the diffraction lobes representing the halo pattern. It should also be noted that the optimization technique of the present invention may be operated on the full expression due to the fact that this expression presents a physical phenomenon and that an image of the light source will physically be maintained. This is described more specifically further below with respect to MTF simulations and measurements of the optimized and non-optimized lenses. To this end the processing may first operate to locate a minimal halo pattern by variation of location of the phase features, to simplify the calculation, the halo pattern may be described by:

$$I_{Halo} = \sum_{n\ne l}\sum_{k\ne l} \tilde{\psi}(\delta x_n - \delta x_k) + \sum_{q\ne l} \tilde{\psi}(\delta x_l - \delta x_q) + \quad \text{(equation 13)}$$

$$\sum_{q\ne l} \tilde{\psi}(\delta x_q - \delta x_l) + \tilde{\psi}(0)$$

$$= \sum_{n\ne l}\sum_{k\ne l} \tilde{\psi}(\delta x_n - \delta x_k) +$$

$$2\sum_{q\ne l} \tilde{\psi}(\delta x_l - \delta x_q) + \tilde{\psi}(0)$$

To minimize this expression, with respect to feature locations, the processing includes deriving of equation 13 with respect to $\delta x_l$ and comparing the derivative to zero:

$$\frac{\partial I_{Halo}}{\partial \delta x_l} = 0 \quad \text{(equation 14)}$$

$$\frac{\partial I_{Halo}}{\partial \delta x_l} = \frac{\partial}{\partial \delta x_l}\left(\begin{array}{l}2\sum_{q\ne l}\sum_m W_l W_q \text{sinc}\left(W_l\frac{m}{\Delta x}\right)\text{sinc} \\ \left(W_q\frac{m}{\Delta x}\right)\exp\left(\frac{2\pi i m(\delta x_l - \delta x_q)}{\Delta x}\right)\end{array}\right)$$

$$= 4\pi i\sum_{q\ne l}\sum_m \frac{m}{\Delta x}W_l W_q \text{sinc}\left(W_l\frac{m}{\Delta x}\right)$$

$$\text{sinc}\left(W_q\frac{m}{\Delta x}\right)\exp\left(\frac{2\pi i m(\delta x_l - \delta x_q)}{\Delta x}\right)$$

providing the result:

$$\sum_m \sum_{q \neq l} \frac{m}{\Delta x} \tilde{\psi}(\delta x_l - \delta x_q) = 0 \quad \text{(equation 15)}$$

Thus, by varying the locations of the features of the first pattern to satisfy equation 15, at least a local minima of the size and intensity of the halo pattern can be found.

Further, the processing may include minimization of the halo pattern with respect to width of the phase features. The processing may thus include calculation of the derivative of the halo pattern with respect to width of the features:

$$\frac{\partial I_{Halo}}{\partial W_l} = 0 \quad \text{(equation 16)}$$

$$\frac{\partial I_{Halo}}{\partial W_l} = \frac{\partial}{\partial W_l} \begin{pmatrix} 2\sum_{q \neq l}\sum_m W_l W_q \mathrm{sinc}\left(W_l \frac{m}{\Delta x}\right) \\ \mathrm{sinc}\left(W_q \frac{m}{\Delta x}\right) \exp\left(\frac{2\pi i m(\delta x_l - \delta x_q)}{\Delta x}\right) + \\ \sum_m W_l^2 \mathrm{sinc}^2\left(W_l \frac{m}{\Delta x}\right) \end{pmatrix}$$

$$= \frac{\partial}{\partial W_l} \begin{pmatrix} 2\sum_{q \neq l}\sum_m \frac{\Delta x^2}{\pi^2 m^2} \sin\left(\pi W_l \frac{m}{\Delta x}\right) \\ \sin\left(\pi W_q \frac{m}{\Delta x}\right) \exp\left(\frac{2\pi i m(\delta x_l - \delta x_q)}{\Delta x}\right) + \\ \sum_m \frac{\Delta x^2}{\pi^2 m^2} \sin^2\left(\pi W_l \frac{m}{\Delta x}\right) \end{pmatrix}$$

$$= \frac{2\Delta x}{\pi} \sum_{q \neq l}\sum_m \frac{\cos\left(\pi W_l \frac{m}{\Delta x}\right)}{m}$$

$$\begin{pmatrix} \sin\left(\pi W_q \frac{m}{\Delta x}\right) \exp\left(\frac{2\pi i m(\delta x_l - \delta x_q)}{\Delta x}\right) + \\ \frac{2}{Q-1} \sin\left(\pi W_l \frac{m}{\Delta x}\right) \end{pmatrix}$$

where Q, appearing in the last line of equation 16, is the number of different phase elements/features along the pattern, e.g. the number of rings in the pattern exemplified in equation 7. The requirement for minimal halo size results with:

$$\sum_{q \neq l}\sum_m \frac{\cos\left(\pi W_l \frac{m}{\Delta x}\right)}{m}\left(\sin\left(\pi W_q \frac{m}{\Delta x}\right)\exp\left(\frac{2\pi i m(\delta x_l - \delta x_q)}{\Delta x}\right) + \right. \quad \text{(equation 17)}$$

$$\left. \frac{2}{Q-1}\sin\left(\pi W_l \frac{m}{\Delta x}\right)\right) = 0$$

It should be noted that additional parameters of the pattern may be varied to located a minimum in the halo size. It should also be noted that according to some embodiments the minimization process includes simultaneous minimization of the halo size with respect to all parameters used, i.e. in this non-limiting example simultaneous solution of equations 15 and 17.

Figure 3A:
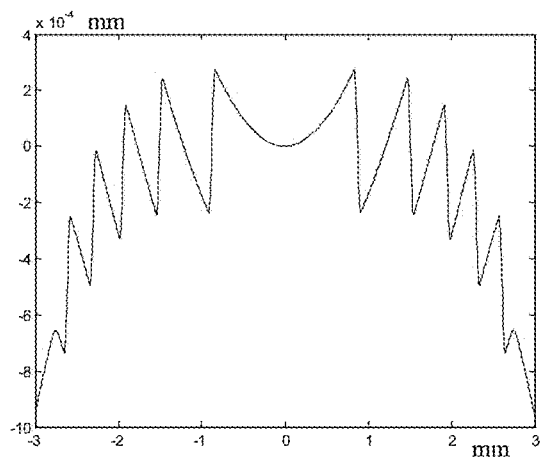
FIG. 3A is a schematic illustration of an example of a lens surface formed with a first pattern (phase pattern) designed to provide specific vision improvement (e.g. EDOF)
Figure 3B:
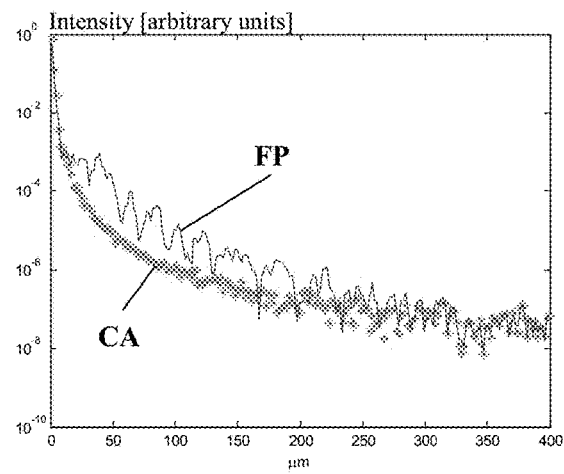
FIG. 3B illustrates the analysis of the first pattern by simulating a halo pattern induced by the lens with the first pattern of FIG. 3A.

The minimization process results in the identified parameter variations providing a second phase pattern that will provide a reduced halo size when used on an optical element (e.g. ophthalmic lens). This is while maintaining the desired vision improvement as provided by the first pattern. FIGS. 3A-3D illustrate an example of a first pattern (FIG. 3A) designed diffractive bi-focal lens with a 1.8 Diopter addition, a halo pattern corresponding to the first pattern FP relative to that of clear aperture CA (FIG. 3B) and a second pattern, generated by minimization of the halo pattern as described above (FIG. 3C) and the corresponding halo pattern SP (FIG. 3D).

As shown FIG. 3A shows a plot of a surface relief first pattern designed to pattern a surface of an ophthalmic lens. The first pattern shown in this non-limiting example is designed to generate an additional power over the original focus of the lens ophthalmic lens, in this example the pattern is designed to introduce an addition of 1.8 Diopter, to thereby generate a bi-focal lens. FIG. 3B shows a simulated halo intensity pattern resulting from light passage through an open clear aperture CA and through a lens carrying the first pattern FP of FIG. 3A. The simulated halo pattern is shown as intensity of the halo (in logarithmic scale) along the vertical axis, relative to radial distance from the optical axis in micrometers (horizontal axis). As shown, light passage through a lens carrying this first pattern provides halo pattern intensity being relatively higher than the halo pattern resulting from light passage through a clear aperture.

Processing of the first pattern (shown in FIG. 3A) according to the above described technique (i.e. introducing variations to features and to the periodicity of the first pattern to minimize halo pattern intensity) generates a second pattern configured to provide the desired vision improvement (bi-focal lens) with reduced halo effect. Such second pattern, being a surface relief pattern to be applied on a surface of an ophthalmic lens is exemplified in FIG. 3C. FIG. 3D shows a simulated comparison between halo pattern intensity generated from light passage through a clear aperture CA and through a lens carrying the second pattern SP of FIG. 3C similar to that of FIG. 3B. As shown in these figures, the halo pattern intensity generated by light passage through a lens having the second pattern is reduced, at least at radial distance greater than ~125 µm from the optical axis, relative to that of the first pattern. Additionally, the halo pattern intensity is reduced almost to the level of clear aperture (i.e. aperture with no pattern at all).

Figure 3C:
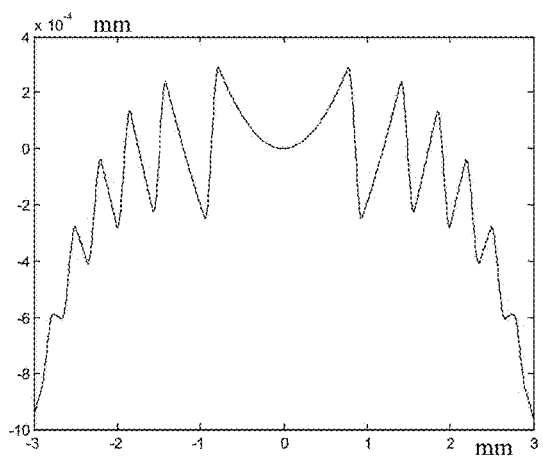
FIG. 3C exemplifies the lens surface of FIG. 3A with the modified second surface pattern designed by altering the feature(s) of the first to reduce the halo pattern.
Figure 3D:
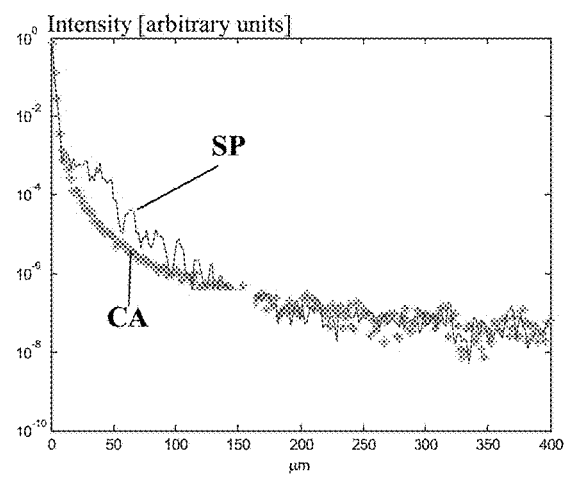
FIG. 3D illustrates analysis of the second pattern by simulating a hallo pattern induced by the lens with the second pattern of FIG. 3C.
Figure 4A:
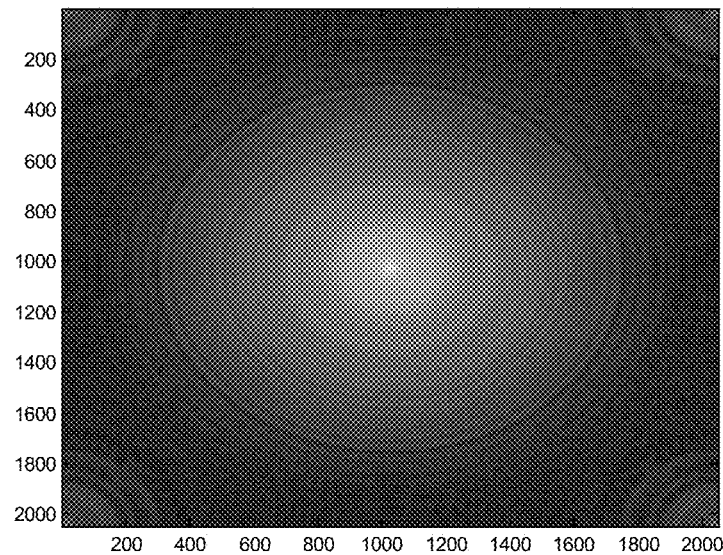
FIGS. 4A-4B illustrate the halo effects for the lens with the first pattern (FIG. 3A) and lens with the second pattern (FIG. 3C) in logarithmic intensity scale.
Figure 4B:
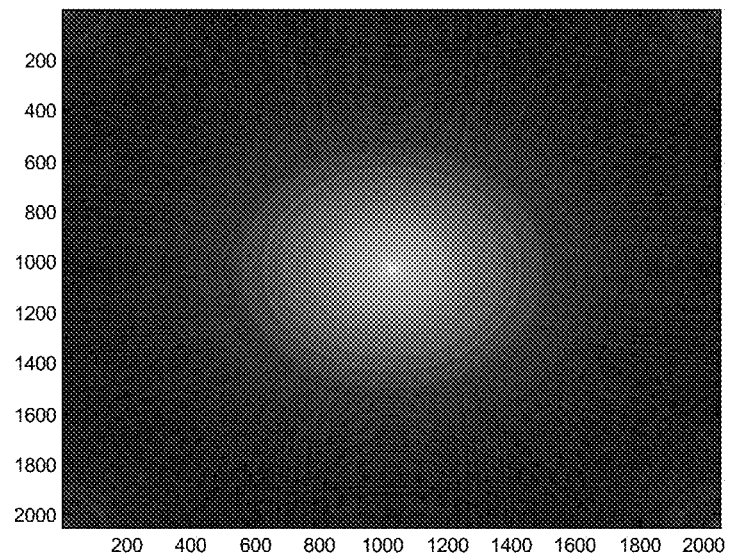

FIGS. 4A and 4B show additional simulated results of the halo pattern generated respectively due to light transmission trough a lens having a first pattern (as shown in FIG. 3A) and a second pattern (as shown in FIG. 3C) in logarithmic scale of intensity. These simulated results are generated according to the halo simulation technique described above, with reference to table 1 and to equations 1-4 above. As seen in these results, the halo pattern is formed by plurality of rings around a central illumination lobe with diminishing intensity. As also shown, the second pattern (FIG. 4B) generates reduced halo pattern, with less rings which are closer to the central lobe relative to the halo pattern generated by the first pattern (FIG. 4A).

Figure 5A:
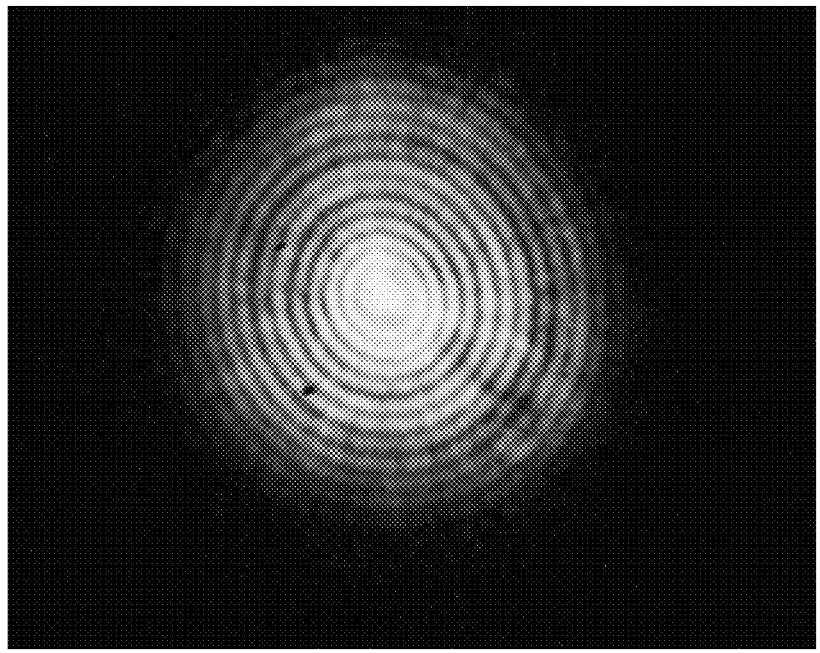
FIGS. 5A-5B show experimental results of measuring the intensity map of light passing through the lens with respectively the first pattern and the second pattern in logarithmic scale.
Figure 5B:
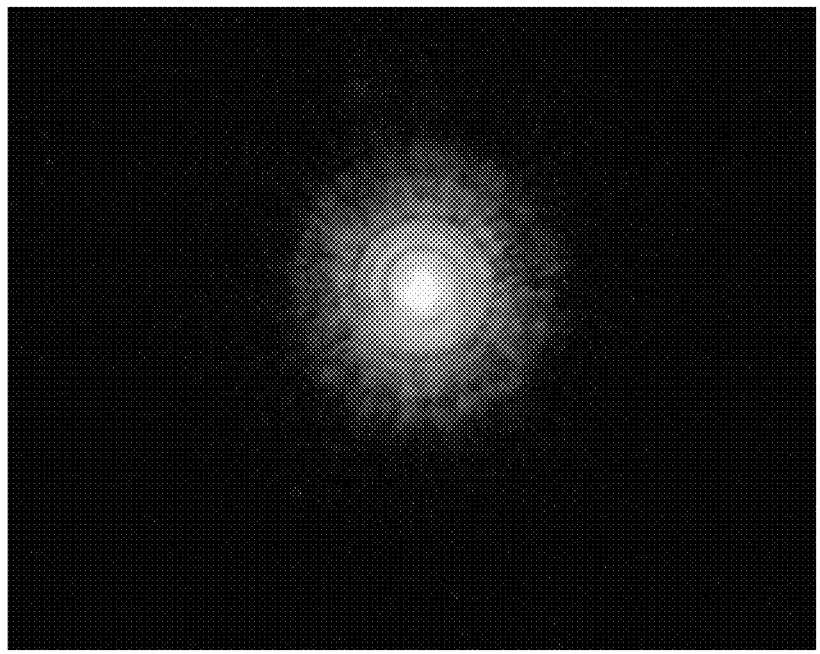

A similar effect is shown in FIGS. 5A-5B showing respectively experimental halo measurement in logarithmic scale corresponding to a lens with a first pattern as shown in FIG. 3A, and to a lens carrying an associated second pattern (i.e. the pattern of FIG. 3B) generated in accordance with the technique of the present invention. These experimental results show how the halo pattern is reduced by intensity and size due to the variations of the first pattern selected to minimize its creation.

Figure 6A:
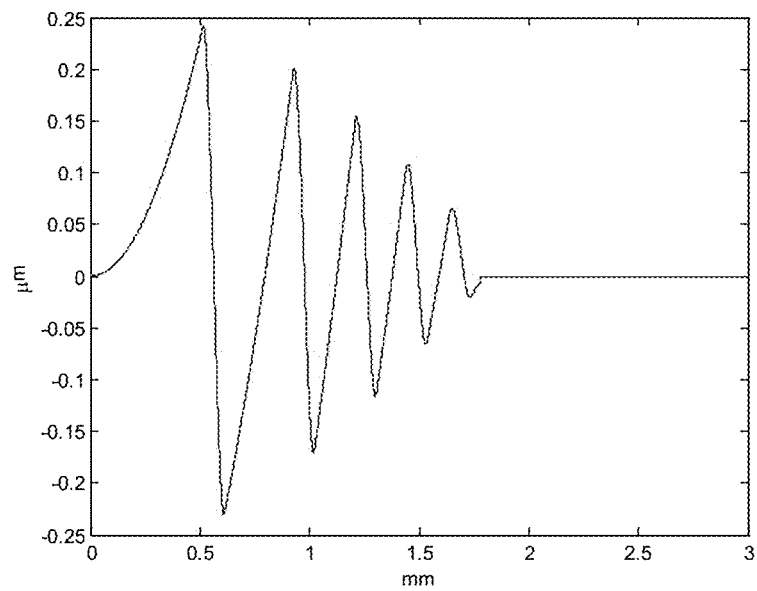
FIGS. 6A-6B show surface profiles of respectively a bi-focal apodized diffractive optical mask to be used with an optical lens and the surface profile after optimization according to the invention.
Figure 6B:
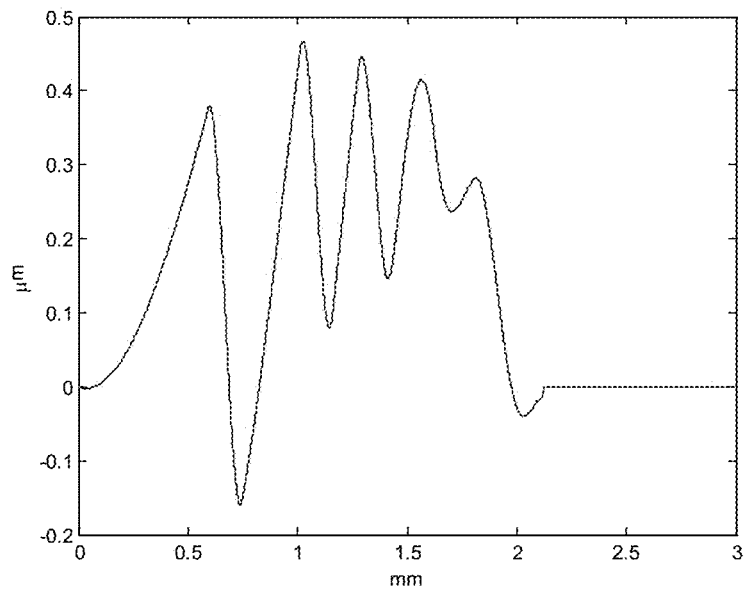

Reference is now made to FIGS. 6A-6B showing one other example of the technique of the present invention. FIGS. 6A-6B illustrate surface profiles of respectively a bi-focal apodized diffractive optical mask (i.e. a mask which is to be incorporated with or attached to an ophthalmic lens) and the surface profile after halo pattern minimization (optimization) according to the technique of the present invention. FIG. 6A exemplifies a surface relief to be patterned on a light collecting surface of an ophthalmic lens, being configured to alter the lens' curvature at different regions thereof in order to provide the lens with bi-focal characteristics. FIG. 6B exemplifies the surface pattern received after optimization of the halo pattern effect to minimize size of the halo pattern. This minimization includes variations of relative size, location and slope of regions as well as different local transitions configured to provide first and second optical powers of the lens. The resulting lens profile of FIG. 6B provides a substantially similar bi-focal characteristic but with reduces size of halo pattern as shown below. It should be noted that the optical masks of FIGS. 6A and 6B are generally configured to be associated with a lens having the same effective aperture. However, in order to reduce a halo pattern, the original design of the mask (FIG. 6A) does not utilize the entire aperture of the lens and covers only a part of the lens. The optimized pattern is configured to reduce the halo effect and can thus utilize a larger portion of the lens' aperture. This provides, in addition to the reduction of the halo pattern, a stronger near vision improvement effect in dark conditions, i.e. when the user's pupils are larger.

Figure 7A:
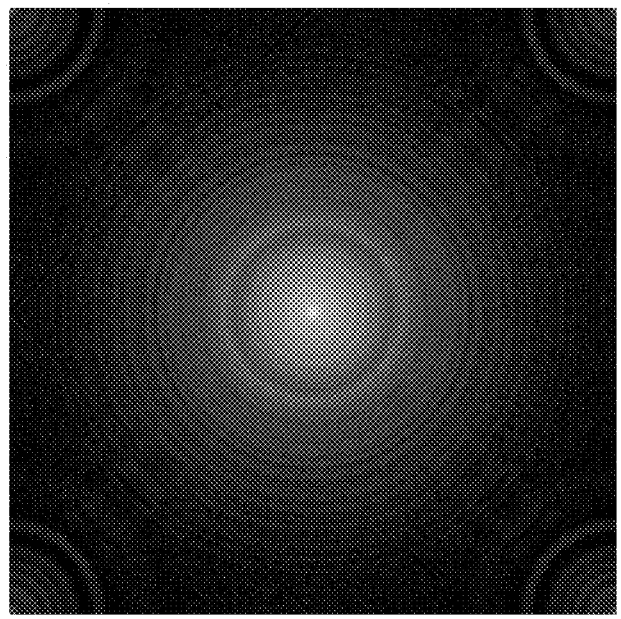
FIGS. 7A-7B show halo pattern simulations corresponding to lens profiles of FIGS. 6A-6B respectively.
Figure 7B:
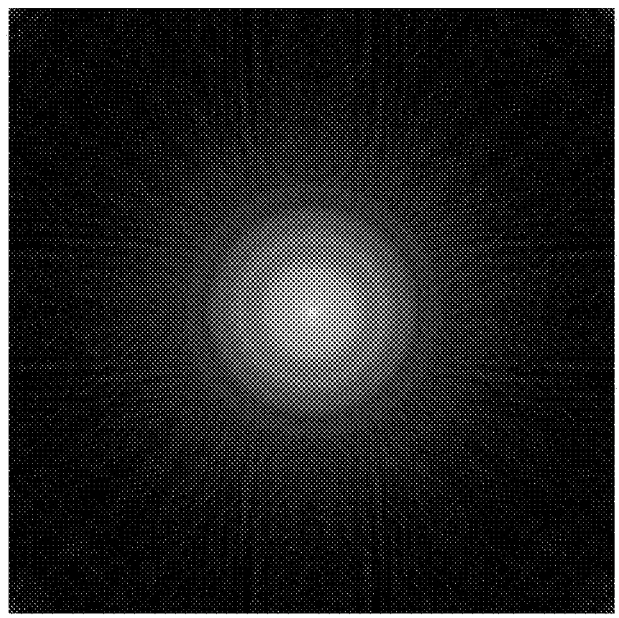
Figure 8A:
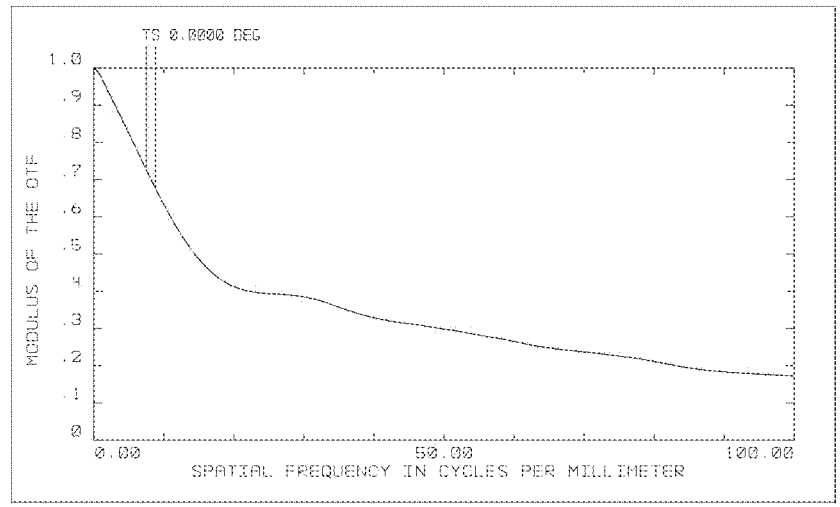
FIGS. 8A-8B show respectively distance MTF measurements at distance of 3 mm EPD for the lens patterns of FIGS. 6A-6B.
Figure 8B:
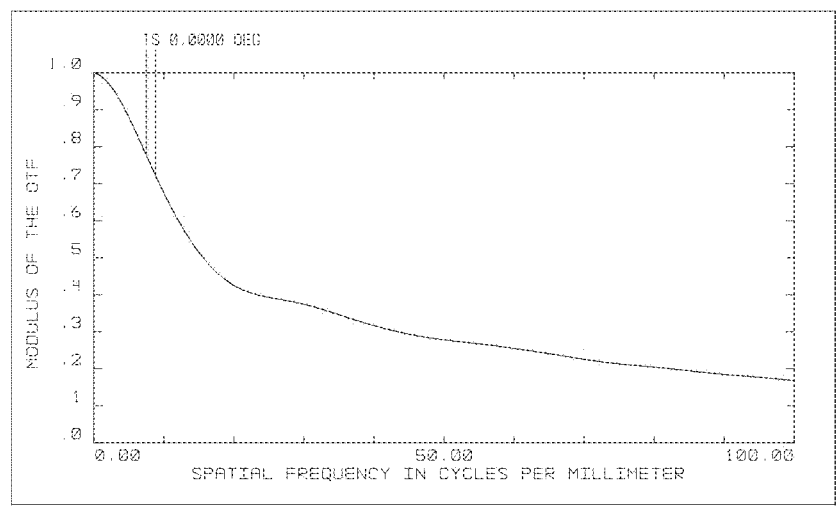
Figure 9A:
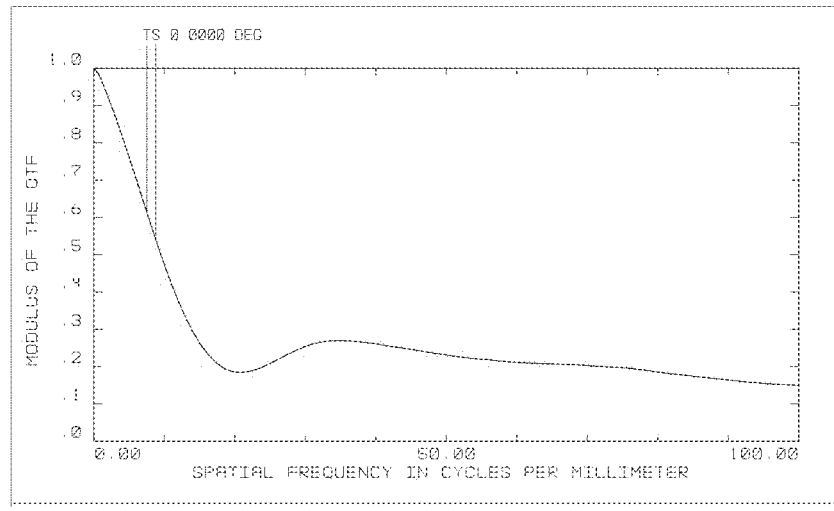
FIGS. 9A-9B show respectively near MTF measurements at distance of 3 mm EPD for the lens patterns of FIGS. 6A-6B.
Figure 9B:
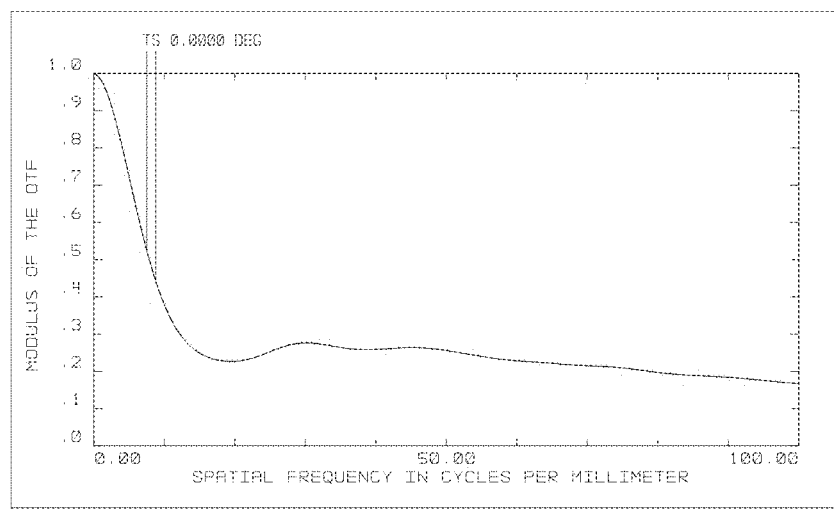
Figure 10A:
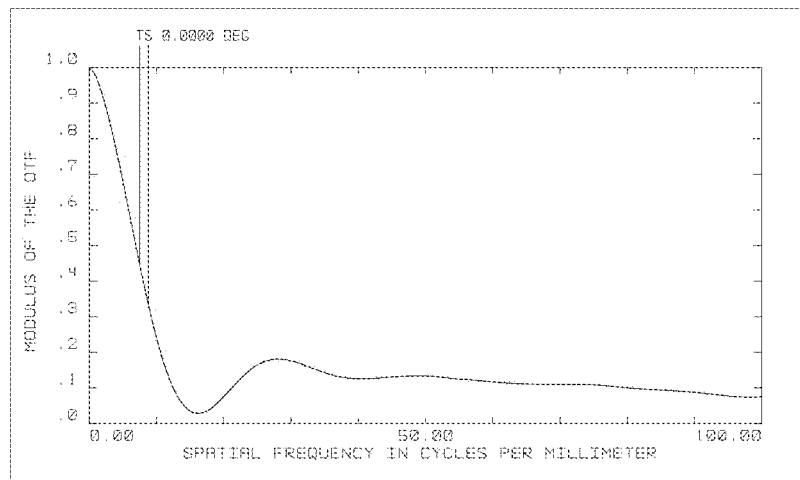
FIGS. 10A-10B show respectively near MTF measurements at distance of 4 mm EPD for the lens patterns of FIGS. 6A-6B.
Figure 10B:
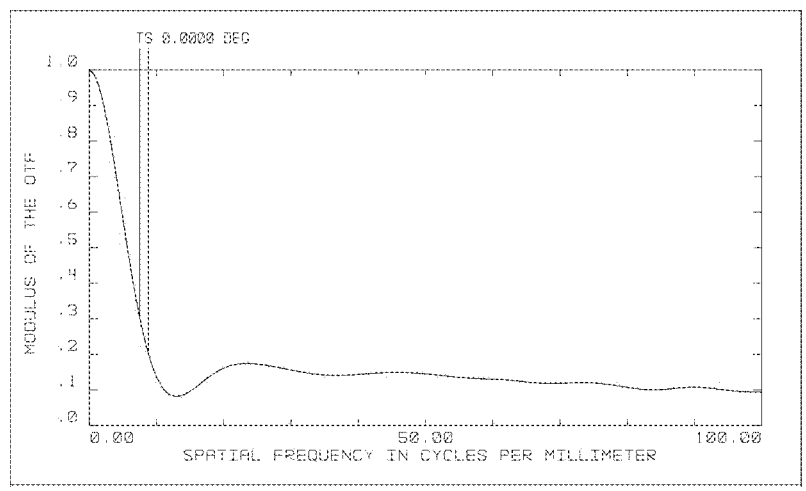
Figure 11A:
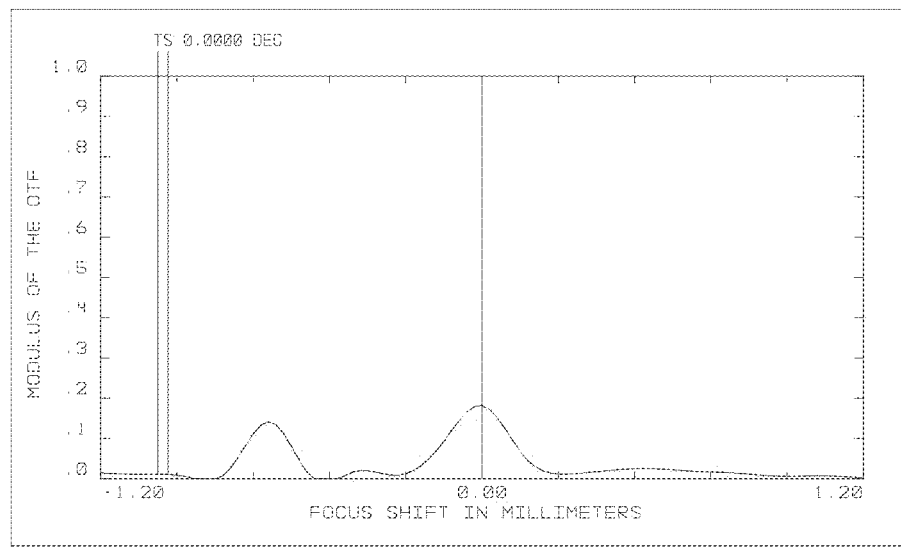
FIG. 11A-11B show respectively through focus MTF measurements for the lens patterns of FIGS. 6A-6B.
Figure 11B:
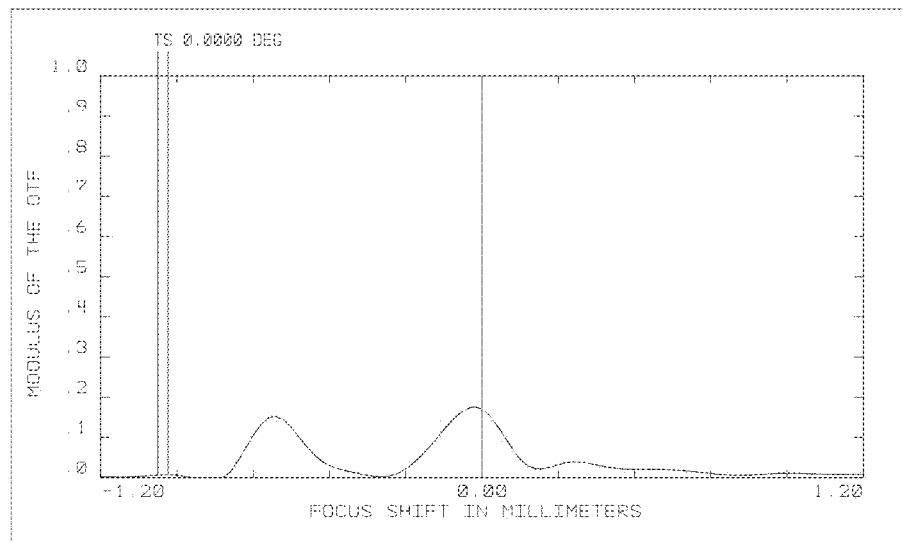

FIGS. 7A-7B, 8A-8B, 9A-9B, 10A-10B and 11A-11B show several simulation results exemplifying the reduction of halo pattern effects as well as the preservation of the intended vision improvement of the lens. FIGS. 7A-7B show respectively simulations of halo pattern caused by light (from a relatively small light source over a dark background) through the lens patterns of FIGS. 6A and 6B. As shown, the resulting halo pattern of the optimized lens profile is reduced after optimization of the lens profile. FIGS. 8A-8B, 9A-9B, 10A-10B and 11A-11B show Modulation Transfer Function (MTF) simulations of the lens patterns of FIGS. 6A-6B respectively. FIGS. 8A-8B show distance (first focal point) MTF measurements at the first focal plane using 3 mm EPD, FIGS. 9A-9B show respectively near (the second focal point) MTF measurements at the second focal plane using 3 mm EPD, FIGS. 10A-10B show respectively near MTF measurements at the second focal plane using f 4 mm EPD and FIGS. 11A-11B show through focus MTF. It should be understood that the first focal plane of the lens is mainly used for improvement of far (distance) vision (i.e. of distant objects) and the second focal plane is mainly used for improvement of near vision (i.e. of objects located near to the eyes). These figures demonstrate that the MTF profile of the lens is substantially maintained after optimization of the pattern according to the present invention. Thus, the technique of the present invention maintains the optical performance of the lens (as prescribed for the patient's vision improvement) at different dimensions of the effective apertures of the lens while reducing the halo pattern. As shown in FIGS. 11A-11B, the overall performance and additional optical power created by the optical design of the first pattern is maintained, i.e. the lens provides an additional focal plane corresponding to optical power of 1.8 Diopter.

Figure 12A:
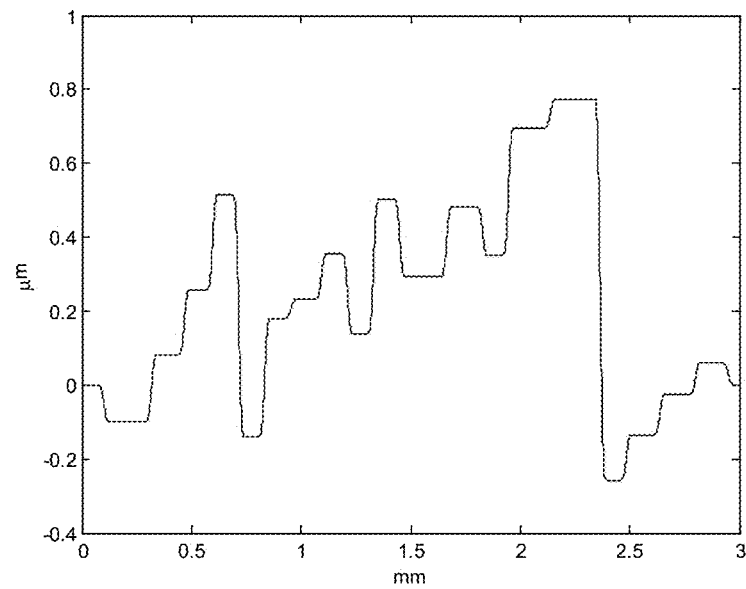
FIGS. 12A-12B illustrate an example of the invention for optimizing a lens with a pattern configured to provide extended depth of focus, where
Figure 12B:
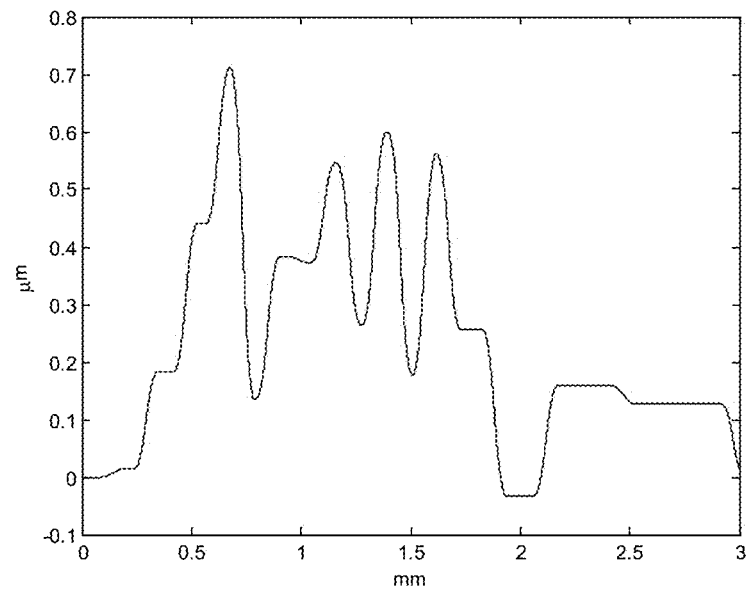

FIGS. 12A-12B, 13A-13B, 14A-14B, 15A-15B, 16A-16B and 17A-17B demonstrate the technique of the present invention when applied to an optical element configured to extend the depth of focus of an ophthalmic lens (i.e. the first, vision improvement pattern is an EDOF pattern). FIGS. 12A-12B exemplify the optimization of the lens with EDOF phase pattern, where FIG. 12A shows the first (original) pattern and FIG. 12B shows the second pattern optimized according to the present invention to reduce the halo effect of the lens with pattern of FIG. 12A. In this example, the EDOF pattern is in the form of a surface relief including a few spaced-apart concentric ring-like phase-affecting features spaced by the lens regions, and the figures show the pattern along the radial axis of the lens.

Figure 13A:
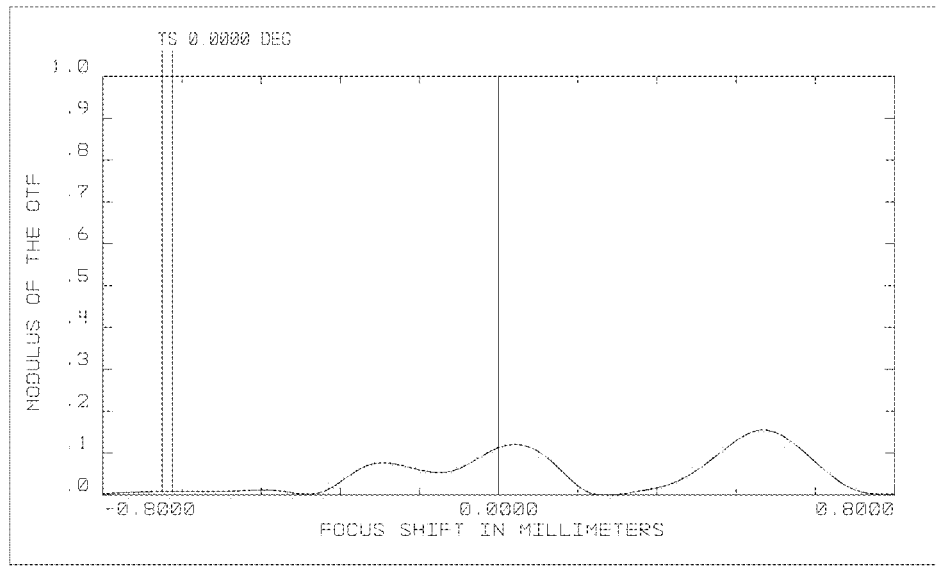
FIGS. 13A-13B show respective through focus MTF measurements for the first EDOF pattern and the second optimized pattern corresponding to the first and second patterns of FIGS. 12A-12B.
Figure 13B:
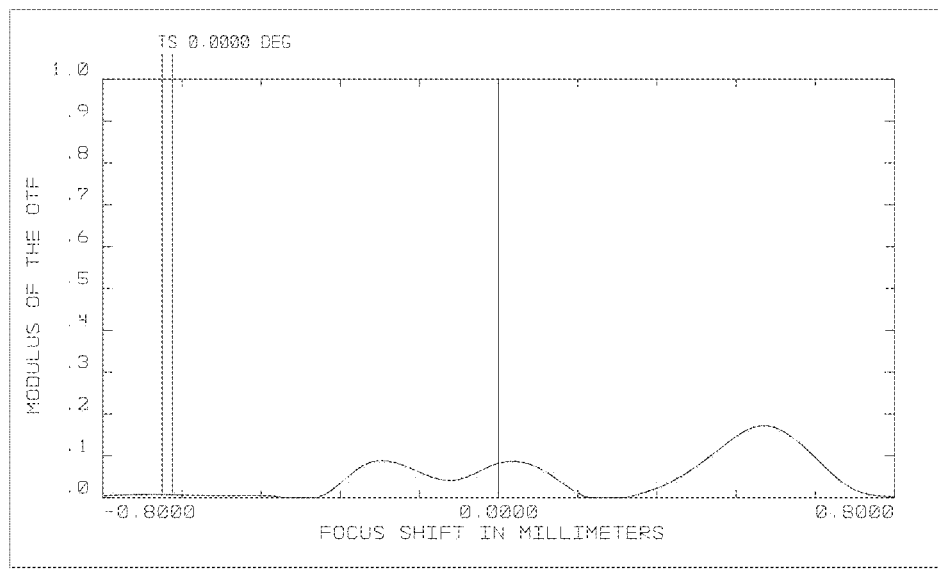
Figure 14A:
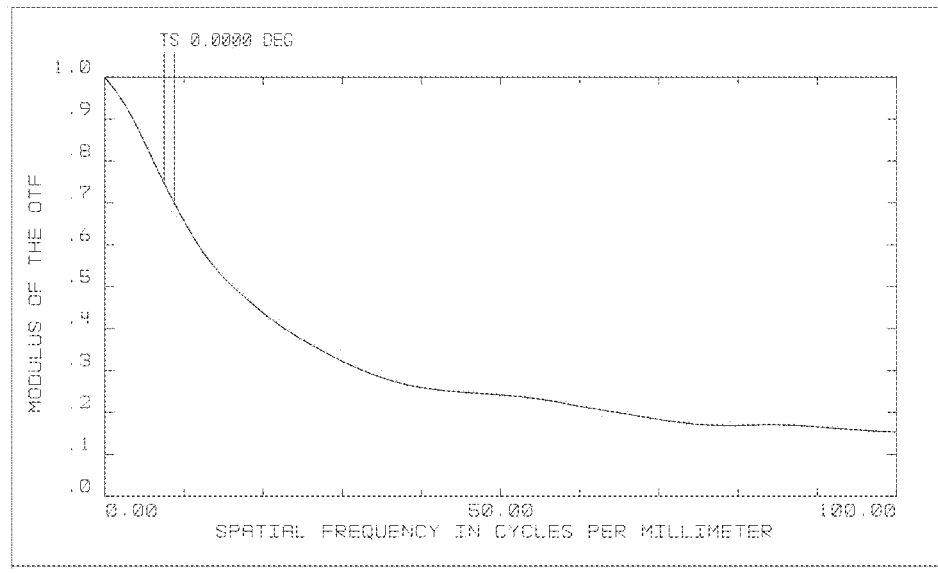
FIGS. 14A-14B show respective distance MTF measurements corresponding to the first and second patterns of FIGS. 12A-12B.
Figure 14B:
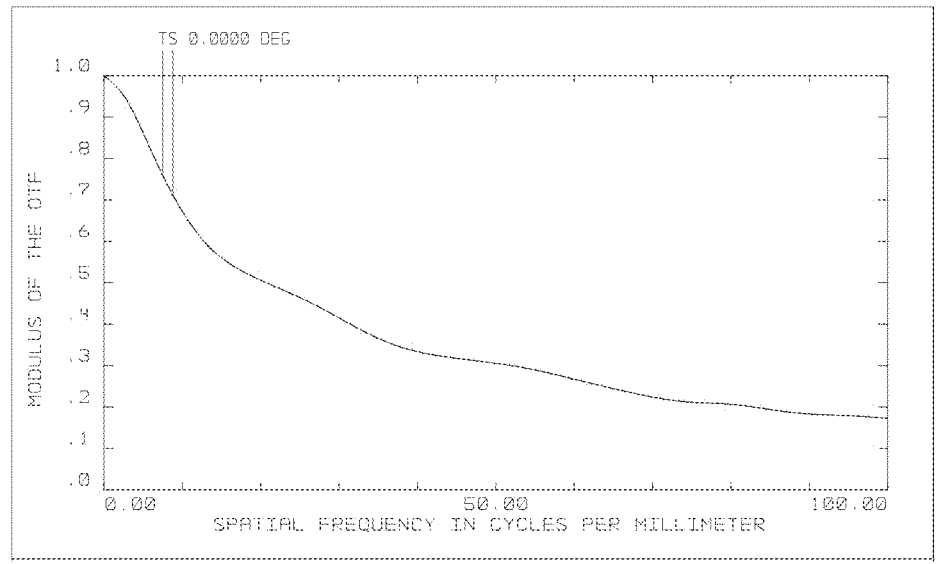
Figure 15A:
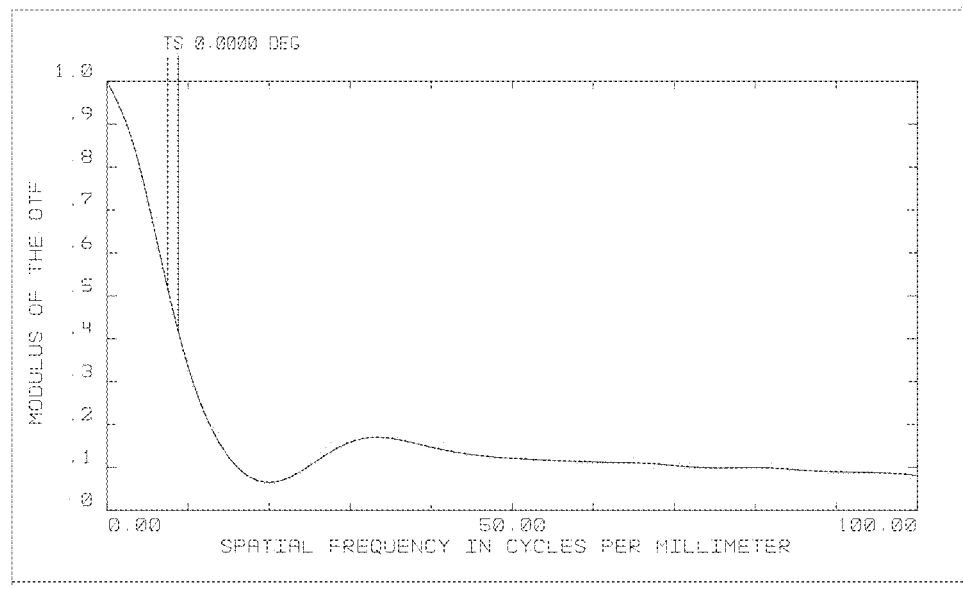
FIGS. 15A-15B show respective 1.5D (intermediate) MTF measurements corresponding to the first and second patterns of FIGS. 12A-12B.
Figure 15B:
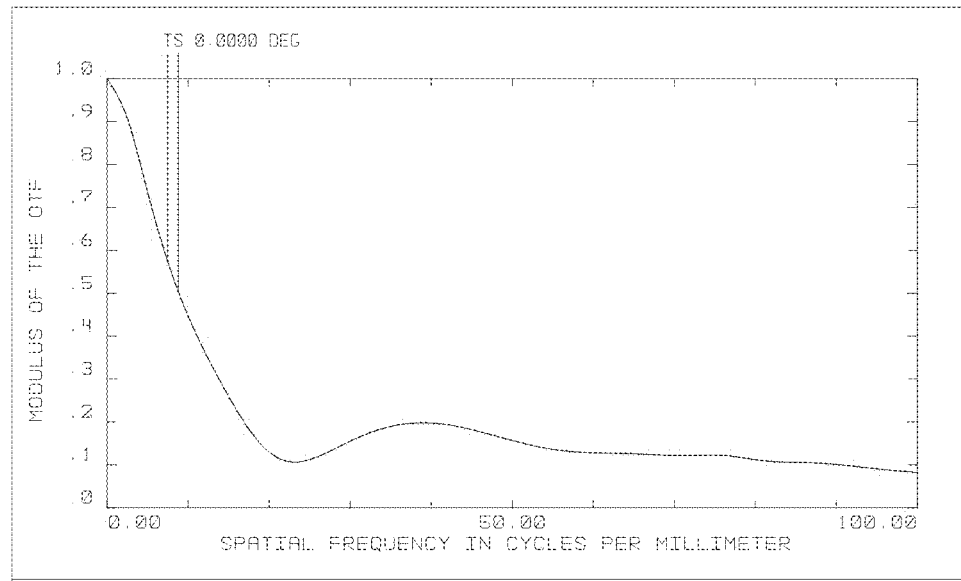
Figure 16A:
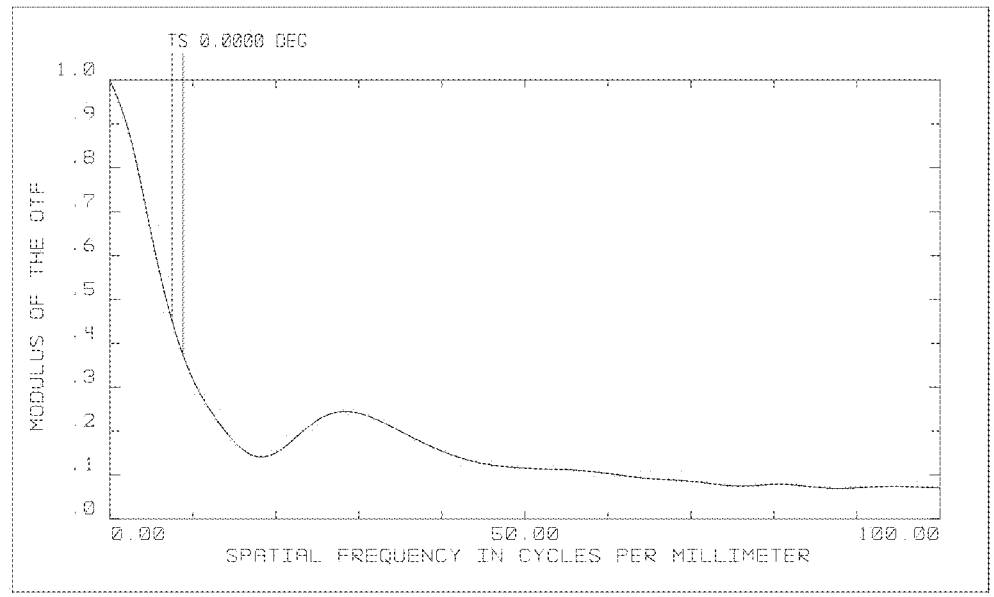
FIGS. 16A-16B show 2.1D (Near) MTF measurements corresponding to the first and second patterns of FIGS. 12A-12B.
Figure 16B:
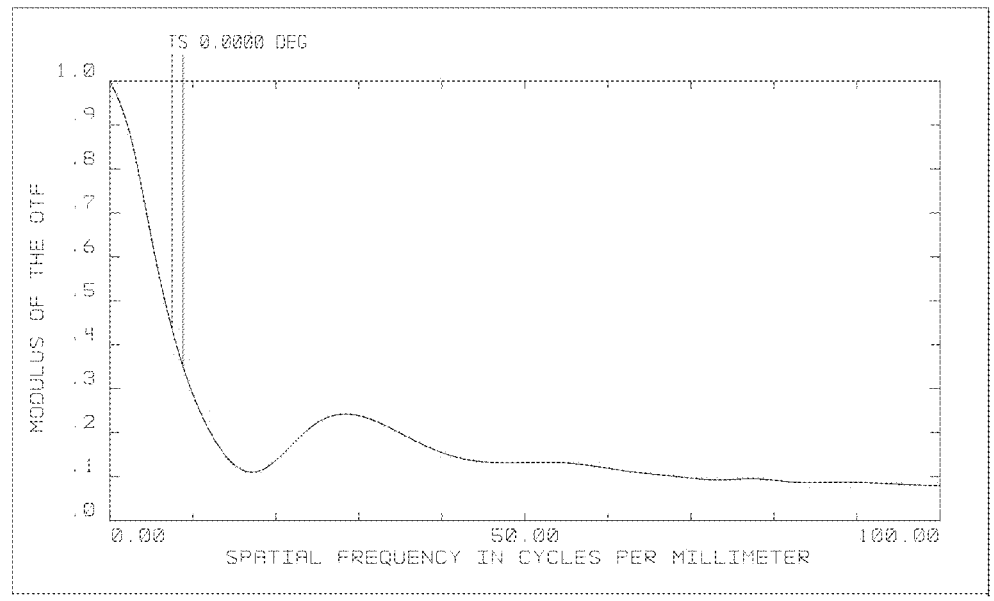
Figure 17A:
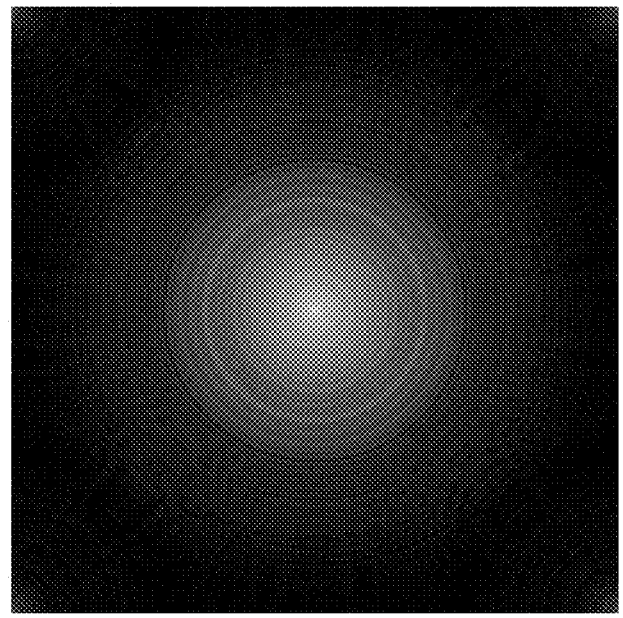
FIGS. 17A-17B show respective halo pattern simulations corresponding to the first and second (optimized) EDOF patterns of FIGS. 12A-12B.
Figure 17B:
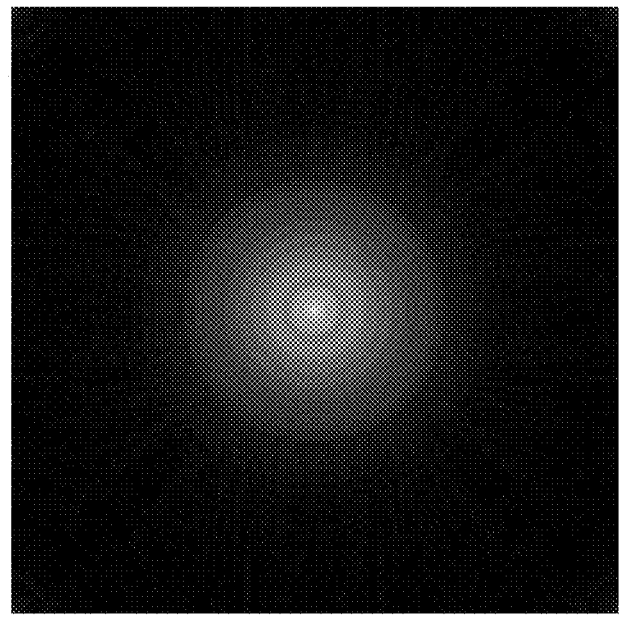

FIGS. 13A-13B, 14A-14B, 15A-15B, 16A-16B illustrate how the optimized (second) pattern maintains the optical performance in the sense of extended depth of focus as well as spatial frequencies, for each discrete axial location. FIGS. 17A-17B show the reduction of the halo effect in the lens with the second pattern as compared to the lens with the first pattern. FIGS. 13A-13B show respective through focus MTF measurements for the first EDOF pattern and the second optimized pattern; FIGS. 14A-14B show respective distance MTF measurements; FIGS. 15A-15B show respective 1.5D (intermediate) MTF measurements; FIGS. 16A-16B show 2.1D (Near) MTF measurements; and FIGS. 17A-17B show respective halo pattern simulations corresponding to the first and second (optimized) EDOF patterns. As shown, the technique of the present invention is based on varying feature(s) of the first pattern to reduce the size of halo pattern while maintaining the optical properties which provide the prescribed vision improvement. As shown, other than the significant reduction in the size of the hallo pattern simulated in FIGS. 17A-17B, the MTF (i.e. optical properties providing the desired vision improvement) is kept substantially similar for various spatial frequencies at the desired locations associated with the optical power and depth of focus provided by the lens and the associated pattern.

Thus, the present invention provides a technique suitable for design of an ophthalmic lens configured to provide prescribed vision improvement with reduced halo pattern. The technique may include variations to one or more pattern and/or feature parameters of a first pattern, designed only to provide appropriate vision improvement, to thereby generate a second pattern maintaining the desired vision improvement while providing reduce halo effect. Those skilled in the art will readily appreciate that various modifications and changes can be applied to the embodiments of the invention as hereinbefore described without departing from its scope defined in and by the appended claims.

The invention claimed is:

1. A method for use in reducing a size of halo effect in an ophthalmic lens, the method comprising:
   providing data indicative of a given ophthalmic lens with a first pattern providing prescribed vision improvement;
   processing said data indicative of the features of the first pattern and generating data indicative of a variation of at least one feature of the first pattern resulting in a second pattern for a same area of the given side of the ophthalmic lens as the first pattern which maintains said prescribed vision improvement and reduces a size of halo effect as compared to that of the ophthalmic lens with the first pattern, wherein the second pattern alters a periodicity of the first pattern; and
   providing the ophthalmic lens with the second pattern at the given side of the ophthalmic lens.

2. The method of claim 1, wherein said processing of said data indicative of the features of the first pattern comprises estimating a halo pattern of the ophthalmic lens with the first pattern.

3. The method of claim 1, wherein said first pattern is configured for extending a depth of focus of the lens.

4. The method of claim 3, wherein the reduction of the size of halo effect is at least 25%.

5. The method of claim 1, wherein said altering of the at least one feature of the first pattern comprises at least one of the following: (i) deviation from a local period of the first pattern; (ii) deviation from a local slope of the first pattern, the local slope being either one of inner and outer slope; (iii) deviation from local maximum height of protrusions in the first pattern; (iv) deviation from local minimum height of protrusions in the first pattern; (v) producing additional, typically highly dense, pattern within one type of features of the first pattern; and (vi) deviation from local pattern position.

6. The method of claim 1, wherein said first pattern is a periodic pattern.

7. The method of claim 6, wherein the second pattern is periodic.

8. The method of claim 1, wherein said providing of the data indicative of the ophthalmic lens with the first pattern comprises using data indicative of at least a dimension of an effective aperture of the lens and data indicative of prescribed vision improvement, and generating data indicative of features of the first pattern to be produced on the lens to thereby provide said prescribed vision improvement.

9. An ophthalmic lens comprising:
a surface pattern being a modification of a first pattern which is configured for providing prescribed vision improvement, at least one of features of said surface pattern being a modification of at least one feature of the first pattern for a same area of the given side of the ophthalmic lens as the first pattern such that said prescribed vision improvement is maintained and a size of halo effect is reduced as compared to that of said lens with the first pattern, wherein the second pattern alters a periodicity of the first pattern.

10. The ophthalmic lens of claim 9, wherein said first pattern is configured for extending a depth of focus of the lens.

11. The ophthalmic lens of claim 9, wherein the reduction of the size of halo effect is at least 25%.

12. The ophthalmic lens claim 9, wherein said modification of the at least one altered feature comprises at least one of the following: (i) deviation from a local period of the first pattern; (ii) deviation from a local slope of the first pattern, the local slope being either one of inner and outer slope; (iii) deviation from local maximum height of protrusions in the first pattern; (iv) deviation from local minimum height of protrusions in the first pattern; (v) producing additional, typically highly dense, pattern within one type of features of the first pattern; and (vi) deviation from local pattern position.

13. The ophthalmic lens of claim 9, wherein said first pattern is a periodic pattern.

14. The ophthalmic lens of claim 13, wherein said surface pattern, being the modification of the first pattern, is periodic.

15. A system for use in designing an ophthalmic lens providing prescribed vision improvement for a patient, the system comprising a control unit comprising data input utility for receiving input data indicative of the patient's vision and desired vision improvement, and a processor utility for processing the input data and generating data indicative of a surface pattern to be produced on the lens, said processing comprising:
analyzing the input data and generating data indicative of a first pattern to be formed on the surface of the lens to provide desired vision improvement;
analyzing data indicative of the lens having said first pattern, evaluating a size of hallo effect of the lens with the first pattern, and generating data indicative of a change in at least one feature of the first pattern resulting in a second pattern for a same area of the given side of the ophthalmic lens as the first pattern which maintains said desired vision improvement and has a reduced size of halo effect as compared to that of said lens with the first pattern,
wherein the second pattern alters a periodicity of the first pattern; and
wherein the system includes patterning equipment for providing the ophthalmic lens with the second pattern at the given side of the ophthalmic lens.

* * * * *